United States Patent [19]

Walts

[11] 4,177,171

[45] Dec. 4, 1979

[54] SHAMPOO

[75] Inventor: John M. Walts, Clark, N.J.

[73] Assignee: Johnson & Johnson, New Brunswick, N.J.

[21] Appl. No.: 628,309

[22] Filed: Nov. 3, 1975

[51] Int. Cl.$^2$ .......................... C11D 1/88; C11D 1/94
[52] U.S. Cl. .................................. 252/541; 252/546; 252/DIG. 1; 252/DIG. 13; 252/DIG. 17
[58] Field of Search .............. 252/541, 546, DIG. 13, 252/DIG. 17, DIG. 1

[56] References Cited

U.S. PATENT DOCUMENTS 3,055,836  9/1962  Masci et al. ..................... 252/546 X

FOREIGN PATENT DOCUMENTS 223814  9/1957  Australia .
598923  5/1960  Canada .

Primary Examiner—Thomas J. Herbert, Jr.

[57] ABSTRACT

An improved non-irritating detergent composition is disclosed. The composition has a high viscosity and good foaming properties. The composition is a mixture of (1) an amphoteric surfactant combined with an anionic surfactant and (2) a nonionic surfactant which is a 16–18 carbon atom fatty monoester of an aliphatic polyhydric alcohol reacted with 60 to 100 moles of ethylene oxide.

3 Claims, No Drawings

SHAMPOO

BACKGROUND OF THE INVENTION

Non-irritating detergent compositions have been known and have been in use for some time. U.S. Pat. Nos. 2,999,069 and 3,055,836 are representative of such prior art non-irritating detergent compositions. These compositions generally comprise an amphoteric surfactant combined with an anionic surfactant and a nonionic surfactant in admixture with other ingredients. The amphoteric-anionic surfactant consists essentially of:

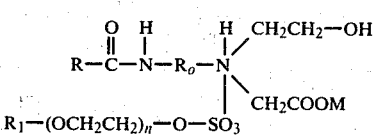

where R is a 9–17 carbon alkyl radical, $R_o$ is an alkylene group of 2–4 carbon atoms, $R_1$ is a member of the group consisting of $C_{13}H_{27}$ and $C_{12}H_{25}$, n is 2–6, and M is a member of the group consisting of alkali metals, triethanolamine, mixtures of an alkali metal with hydrogen and mixtures of triethanolamine with hydrogen. The nonionic surfactant portion of the composition is usually a derivative of a 9–18 carbon atom fatty acid monoester of an aliphatic polyhydric alcohol reacted with 10–20 moles of ethylene oxide.

These prior art compositions, although they are non-irritating and have good foaming characteristics, have very low viscosities. Increasing the viscosity of the compositions by employing viscosity building additives or thickeners results in a deterioration of the foaming characteristics of the compositions.

Increased viscosity without foam degeneration is desirable in order to formulate detergent compositions, especially non-irritating shampoo compositions, that may be marketed as concentrates in tube type containers. The tubed type formulations have found wide acceptance with consumers because of the inherent ease and control of the application of such high viscosity formulations to the hair. However, no tube formulations of the non-irritating type shampoo currently exist in the marketplace.

SUMMARY OF THE PRESENT INVENTION

In formulating detergent compositions of the type discussed, I have discovered that by selecting a particular group of fatty acids as the fatty acid portion of the nonionic surfactant and reacting the resultant monoester with a relatively high mole ratio of an alkylene oxide, it is possible to obtain detergent formulations of high viscosity, that is, greater than 4000 centipoise, at 22°–25° C., and which are also non-irritating and have excellent foaming properties.

The particular fatty acids which I have found to produce this result are those containing 16 to 18 carbon atoms. These include acids such as palmitic acid, stearic acid, isostearic acid and the like.

These fatty acids are reacted with a polyhydric alcohol to form an hydrophobic ester and subsequently reacted with an alkylene oxide to produce the hydrophilic portion of the surfactant composition. The number of oxyalkylene units added to an ester molecule is between about 60 and 100. An oxyalkylene content generally below about 60 units will not result in the increased viscosity of the composition that is desired. Increasing the oxyalkylene content above about 100 units does not result in any improvement in the properties of the composition over those obtained at an oxyalkylene content level of 100.

The reaction of the fatty acid with the polyhydric alcohol to form the ester and the addition of the oxyalkylene groups can be carried out by well-known methods.

Generally, the polyoxyalkylene compounds are prepared by dehydration of known carbohydrates, preferably a 4 to 6 carbon atom carbohydrate, such as sorbitol to sorbitan in known fashion according to the following equation:

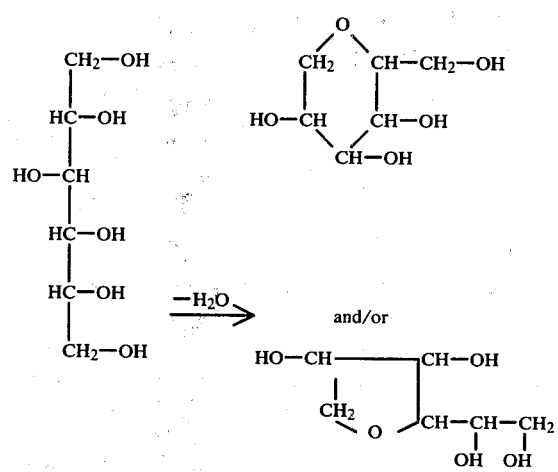

The sorbitan is then esterified with a fatty acid to produce an ester as follows:

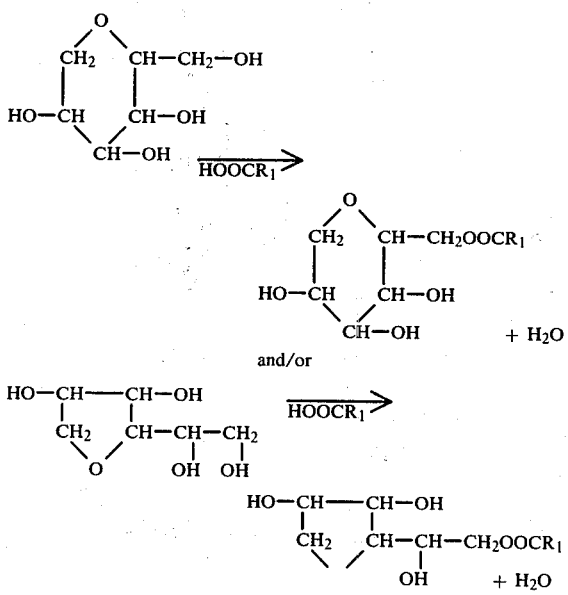

The latter product is then treated with alkylene oxide under known conditions with the resultant introduction of long oxyalkylene chains at the hydroxyl groups. The usual alkylene oxide used is ethylene oxide although propylene oxide or a mixture of both may be used.

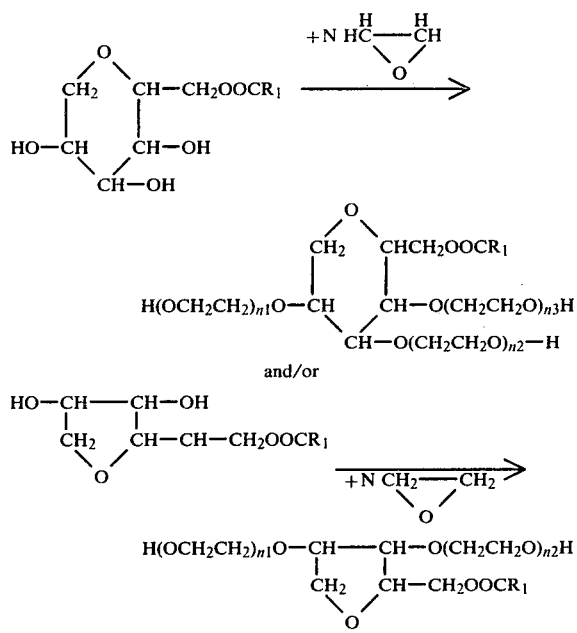

The total number N of oxyalkylene groups introduced per molecule is the sum of $n_1+n_2+n_3$. In the present composition, the total number of oxyalkylene units is between 60 and 100. The alkyl groups $R_1$, are those having either 16 or 18 carbon atoms or an admixture of both.

The nonionic surfactant that is preferred is sorbitan monopalmitate having 80 moles of ethylene oxide.

The amphoteric surfactant in combination with the anionic surfactant that is preferred in the present composition is one of the formula:

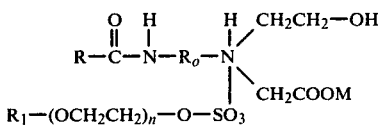

where R is a 9–17 carbon alkyl radical, $R_o$ is an alkylene group of 2–4 carbon atoms, $R_1$ is a member of the group consisting of $C_{13}H_{27}$ and $C_{12}H_{25}$, n is an intreger from 2 to 6, M is a member of the group consisting of the group of alkali metals, hydrogen, triethanolamine, mixtures of an alkali metal with hydrogen and mixtures of triethanolamine with hydrogen. The method of forming these compounds is taught in U.S. Pat. No. 2,781,384.

In the reaction products of the formation of the amphoteric surfactant there may also be present some amount of the compound of the formula:

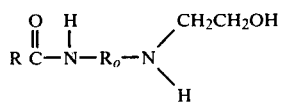

which when reacted with the anionic surfactant forms:

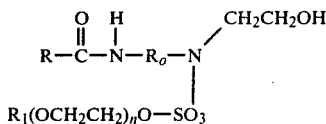

The relative amounts of the amphoteric-anionic surfactant that may be used in the final formulation is from about 5 to about 20%, by weight, based on the total weight of the composition. The preferred amounts being from 5 to 10%. The nonionic surfactant may be present in an amount of from 8 to 20% by weight of the total weight of the composition. The preferred amounts being from 14 to 20%. The other ingredients in the formulation may include other surfactants, water, stabilizers, additional thickeners, dyes and an acid such as hydrochloric acid to neutralize the formulation. Other ingredients commonly used in detergent formulations may also be present.

In the following Examples, the irritation test employed was the following modified Draize test (See J. H. Draize, et al., Toilet Goods Associations #17, May, 1952, #1 Proc. Sci. Sect.):

A 0.1 ml. of the undiluted sample of the neutral composition under test is dropped into one eye of each of six rabbits. Daily administration of the same quantity of each of the samples is continued for 3 consecutive days. Observations are recorded after one hour, one day, two days, three days, four days and seven days after samples are dropped into the eyes. The extremes of the results either show substantially no change or show only a slight irritation (foreign body effect) in the appearance of the rabbits' eyes after seven days or severe irritation or complete corneal opacity, as the case may be.

The foam levels in the following examples were measured by the following modification of the well-known Ross-Miles foam test ["Oil and Soap", 18, 99–102 (1941)]:

(1) Lanolin, anhydrous, cosmetic grade is mixed with dioxane (technical grade) in the proportion of 2.5 grams lanolin and 100 grams of dioxane. The lanoline is first mixed with 25 ml. of dioxane. This mixture is heated over a stream bath to 45° C. in order to dissolve the lanolin in the dioxane. The remainder of the dioxane is then added and mixed. This lanolin-dioxane solution, which is stored in an amber bottle, should be prepared fresh on the day before the tests are run and should be aged at low temperatures for 12 to 24 hours before testing begins.

(2) The shampoo to be tested is diluted by adding 376 cc. of distilled water (room temperature) to 4 grams of the shampoo, and then adding 20 cc. of the lanoline-dioxane solution described in (1) above while mixing.

(3) The final solution of shampoo, water, dioxane, and lanolin described in (2) is then run in the Ross-Miles foam column in the usual way. All tests are conducted in duplicate, and the average of the two results is taken.

(4) Foam stability is determined by measuring the decay in foam height after five minutes, expressed as a percentage of the original height.

EXAMPLES 1–6

Six detergent formulations were prepared from aqueous solutions of an amphoteric-anionic surfactant complex and nonionic surfactants. The amphoteric portion of the surfactant was:

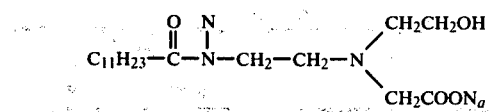

and was reacted with sodium tridecyloxydiethyleneoxyethyl sulfate as set forth in U.S. Pat. No. 2,781,384.

The nonionic portion of the surfactant system was either the stearate or palmitate or laurate ester of sorbitan reacted with either 20 or 80 moles of ethylene oxide. The amounts of the amphoteric-anionic surfactant, shown as a 37% active aqueous solution, and the nonionic surfactant 100% active, are shown in grams in Table I. The pH of each composition was adjusted to 7.0±0.1 by the addition of hydrochloric acid. Sufficient deionized water was added to each samples so that the total sample weighed 100 grams. The viscosity of each sample was determined by the Brookfield method. The samples were also tested for initial foaming and the percentage decay of the foam after five minutes by the modified Ross-Miles method heretofore described.

content as indicated in Table II. The basic formulation was as follows as indicated below, with the amounts of ingredients given in grams:

| | |
|---|---|
| Amphoteric-Anionic Surfactant as in Example I (34% aqueous solution) | 301 |
| Nonionic Surfactant | 126 |
| Deionized Water | 400 |
| Acid Solution pH adjustment | 25 |
| Dye and Perfume | 7 |
| Sorbitan Monolaurate | 9 |
| Polethylene glycol distearate | 20 |
| Additional Water to 1000 grams | q.s. |

The sorbitan monolaurate is a conditioner. The polyethylene glycol distearate is a thickner, which when added in small amounts to a composition of the present invention does not result in a significant reduction in foaming properties.

TABLE I

| Example | 1 | 2 | 3 | 4 | 5 | 6 |
|---|---|---|---|---|---|---|
| Amphoteric/anionic complex | 30.1 | 30.1 | 30.1 | 30.1 | 30.1 | 30.1 |
| Sorbitan monostearate 20 moles ethyleneoxide | 12.6 | | | | | |
| Sorbitan monopalmitate 20 moles ethyleneoxide | | 12.6 | | | | |
| Sorbitan monolaurate 20 moles ethyleneoxide | | | 12.6 | | | |
| Sorbitan monostearate 80 moles ethyleneoxide | | | | 12.6 | | |
| Sorbitan monopalmitate 80 moles ethyleneoxide | | | | | 12.6 | |
| Sorbitan monolaurate 80 moles ethyleneoxide | | | | | | 12.6 |
| Deionized H$_2$O qs | 100 | 100 | 100 | 100 | 100 | 100 |
| pH | 7.02 | 7.01 | 7.01 | 7.02 | 7.02 | 7.00 |
| Viscosity (cps) | 7.2 | 7.8 | 8.8 | 10,120 | 4,120 | 123 |
| Ross Miles Foam Initial | 85 mm | 82 mm | 99 mm | 102 mm | 107 mm | 119 mm |
| 5 Minute Decay | 25% | 13% | 18% | 5.9% | 7.5% | 2.5% |

EXAMPLES 1-6 show the effect on viscosity and foaming characteristics by the increased polyoxyethylene content of the nonionic surfactant component of the composition. A comparison of Example 4 or 5 with Example 6 show the effect of using the 16 to 18 carbon atom fatty acid on increasing viscosity without significant decreasing initial foam and foam decay.

EXAMPLES 7-14

A series of eight shampoo formulations were prepared in which the nonionic portion of the formulation was varied. Examples 17-10 were formulated with sorbitan monostearate having an ethylene oxide content as indicated in Table II. Examples 11-14 were formulated with sorbitan monopalmitate having an ethylene oxide

TABLE II

| | | | Ross Miles Foam | |
|---|---|---|---|---|
| Example | Moles Ethyleneoxide | Viscosity (cps) | Initial (mm) | 5 Min Decay(mm) |
| 7 | 20 | 3300 | 96 | 40 |
| 8 | 60 | 17500 | 112 | 103 |
| 9 | 80 | 24850 | 115 | 106 |
| 10 | 100 | 23450 | 121 | 110 |
| 11 | 20 | 2000 | 96 | 53 |
| 12 | 60 | 11800 | 115 | 101 |
| 13 | 80 | 16300 | 117 | 105 |
| 14 | 100 | 14250 | 118 | 112 |

EXAMPLES 15-18

A series of detergent formulations having increasing amounts of thickening agent were prepared. These Examples demonstrate that the addition of increasing amounts of a thickening agent does not significantly increase the viscosity of the formulation but does depress the foaming quality of the formulation. All the 5 formulations were prepared employing a base of the following formulation.

| Base Formulation | |
|---|---|
| Deionized Water | 800 grams |
| Amphoteric-Anionic Surfactant as in Example 1 (34% aqueous solution) | 602 grams |
| Nonionic surfactant, Sorbitan monolaurate 20 moles ethylene oxide | 252 grams |
| Additional Deionized water was added to a total weight of the base formulation to 1800 grams. The pH was adjusted to 7.1. | |

To 90 grams base formulation varying amounts of polyethylene glycol distearate (PEG 6000) were added. The viscosity and the foam characteristics were determined and the results are shown in Table III.

TABLE III

| EXAMPLE | PEG 6000 | Viscosity cps 70° F. | Ross Miles Foam Initial mm | Final mm |
|---|---|---|---|---|
| 15 | 0 | 1 | 134.5 | 129.5 |
| 16 | 2 grams | 145.0 | 121.0 | 118.0 |
| 17 | 6 grams | 1960.0 | 110.0 | 72.5 |
| 18 | 9 grams | 3480 | 109.5 | 71.0 |

EXAMPLES 19-20

Two detergent formulations in the form of shampoos were prepared with the following ingredients: (amounts are listed in percent by weight)

| | EXAMPLES | |
|---|---|---|
| | 19 W/W % | 20 W/W % |
| Amphoteric - anionic surfactant (1) | 30.1 | 30.1 |
| Deionized water | 30.0 | 30.0 |
| Nonionic surfactant (2) | 14.0 | 20.0 |
| Preservative System | 0.6 | 0.6 |
| Dye and Perfume | 0.7 | 0.7 |
| Deionized water | q.s. | q.s. |
| | 100% | 100% |

| | EXAMPLES | |
|---|---|---|
| | 19 W/W % | 20 W/W % |
| Viscosity cps 22° C. | 12,800 | 19,900 |

(1) Same as Example 1, 34% aqueous solution
(2) Sorbitan monostearate - 80 moles ethylene oxide Each formulation was tested for irritation and found to have low ocular irritation.

EXAMPLE 21

A detergent formulation in the form of a shampoo was prepared with the following ingredients: (amounts are in grams)

| | Grams |
|---|---|
| Amphoteric-anionic surfactant (1) | 301.0 |
| Amphoteric surfactant (2) | 200.0 |
| Nonionic surfactant (3) | 200.0 |
| Deioniozed water | 100.0 |
| Preservative system | 5.0 |
| Dye and Perfume | 8.3 |
| Deionized water q.s. | 1100 |

(1) Same as in Example 1, 34% aqueous solution
(2) N-lauroyl-N' sodium carboxymethyl-N' (2-hydroxyethyl) ethylenediamine
(3) Sorbitan monopalmitate - 80 moles ethyleneoxide The formulation was tested for irritation by the modified Draize Test and found to have low ocular irritation.
What I claim is:

1. A low irritation shampoo composition having a viscosity greater than 4,000 centipoise as measured at 23°-25° C. comprising;
   (a) 5-20% by weight, based on the total weight of the composition, of an amphoteric anionic surfactant of the formula

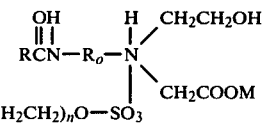

where R is a 9-17 carbon alkyl radical, $R_o$ is an alkylene group of 2-4 carbon atoms, $R_1$ is a member of the group consisting of $C_{13}H_{27}$ and $C_{12}H_{25}$, n is 2-6, and M is a member of the group consisting of alkali metals, triethanolamine mixtures of an alkali metal with hydrogen and mixtures of triethanolamine with hydrogen, and
   (b) 8 to 20% by weight of a 16-18 carbon atom fatty acid monoester of sorbitan reacted with 60 to 100 moles of ethylene oxide.

2. The composition of claim 1 in which the fatty acid monoester is sorbitan monopalmitate.

3. The composition of claim 1 in which the fatty acid monoester is sorbitan monostearate.

* * * * *